United States Patent
Knezevich et al.

(10) Patent No.: US 8,697,104 B2
(45) Date of Patent: Apr. 15, 2014

(54) APPARATUS, SYSTEM, AND METHOD FOR CREATING IMMUNOLOGICALLY ENHANCED SPACES IN-VIVO

(76) Inventors: Charles Knezevich, Spring Valley, CA (US); Robert Silvetz, San Diego, CA (US)

( * ) Notice: Subject to any disclaimer, the term of this patent is extended or adjusted under 35 U.S.C. 154(b) by 644 days.

(21) Appl. No.: 12/715,052

(22) Filed: Mar. 1, 2010

(65) Prior Publication Data

US 2010/0272772 A1 Oct. 28, 2010

Related U.S. Application Data

(60) Provisional application No. 61/156,498, filed on Feb. 28, 2009, provisional application No. 61/253,077, filed on Oct. 20, 2009.

(51) Int. Cl.
| | | |
|---|---|---|
| *A61K 39/00* | (2006.01) | |
| *A61K 39/02* | (2006.01) | |
| *A61K 39/12* | (2006.01) | |
| *A61K 9/00* | (2006.01) | |
| *A61P 35/00* | (2006.01) | |
| *A61P 31/04* | (2006.01) | |
| *A61P 31/12* | (2006.01) | |

(52) U.S. Cl.
USPC ........ 424/422; 424/423; 424/426; 424/184.1; 424/204.1; 424/234.1; 424/277.1

(58) Field of Classification Search
None
See application file for complete search history.

(56) References Cited

U.S. PATENT DOCUMENTS

| | | |
|---|---|---|
| 5,964,804 A | 10/1999 | Brauker et al. |
| 6,156,305 A | 12/2000 | Brauker et al. |
| 6,159,143 A | 12/2000 | Lennox |
| 6,203,787 B1 | 3/2001 | Thompson et al. |
| 6,344,445 B1 * | 2/2002 | Boursnell et al. ........... 514/44 R |
| 7,087,712 B1 * | 8/2006 | Brossart et al. ............... 530/300 |
| 2002/0077676 A1 | 6/2002 | Schroeppel et al. |
| 2004/0166141 A1 * | 8/2004 | Cerami et al. ................ 424/426 |

OTHER PUBLICATIONS

Begley et al., "Targeted Therapies to Improve Tumor Immunotherapy," *Clinical Cancer Research*, Jul. 15, 2008, vol. 14, No. 14, pp. 4385-4391.
Yagita et al., "TRAIL and its receptors as targets for cancer therapy," *Cancer Science*, Oct. 2004, vol. 95, No. 10, pp. 777-783.

* cited by examiner

*Primary Examiner* — Karen Canella
(74) *Attorney, Agent, or Firm* — Saliwanchik, Lloyd & Eisenschenk

(57) ABSTRACT

The present invention creates an immunologically protected/enhanced space in viva in a mammal by removing the impact of soluble inhibitors of the mammal's immune system in a defined space within the body. Placing an antigen source within the defined protected space along with a monocyte-containing blood sample from the mammal being treated and a dendritic cell-inducing factor allows a dendritic-antigen presentation process to proceed to completion. The protected/enhanced space is created by surrounding the protected space with ligands which absorb and/or bind to one or more soluble inhibitors. The implant can be loaded with a patient's cancer cells to treat cancer.

72 Claims, 4 Drawing Sheets

APPARATUS, SYSTEM, AND METHOD FOR CREATING IMMUNOLOGICALLY ENHANCED SPACES IN-VIVO

CROSS-REFERENCE TO RELATED APPLICATIONS

The present application claims priority under 35 U.S.C. §119(e) to U.S. Provisional Applications No. 61/156,498, filed on Feb. 28, 2009, and 61/253,077 filed on Oct. 20, 2009, the disclosures of which are incorporated herein by reference in their entireties.

FIELD OF THE INVENTION

The present invention relates to medical devices, systems and methods to create an immunologically enhanced or protected space in vivo in a mammal to allow the mammal's immune system to function properly in the identification and handling of antigens. In particular, the immunologically protected/enhanced space allows the process of antigen presentation by induced dendritic cells to proceed to completion for the purposes of combating infection, inducing anti-tumor vaccination or dampening autoimmunity, in-vivo, by removing the impact of soluble inhibitors of the immune system.

BACKGROUND OF THE INVENTION

Every year, across the world, 12 million individuals get cancer of which about 7.5 million will die. Under current trends, by year 2010 cancer will become one of the leading single causes of death worldwide.

Current cancer therapies using chemotherapeutic agents and radiation beyond stage 3 cancer are an abject failure. Beyond stage 3 cancer, these strategies often buy the patient only some extra time; but this comes at the heavy cost of extreme suffering and reduction in quality of life for the majority of patients.

In private, many cancer experts suggest that the most promising approach for the future in treating cancers is through the control of the immune system. Clinically verified cases of spontaneous remission exist, suggesting that the failure of the immune system to generate a proper response is central to the problem of cancer. The body fails to generate a functional vaccine against the cancer allowing the cancer to grow uncontrollably.

Elevated concentrations of various cytokines, cytokine receptors, and gangliosides (glycosphingolipids), are known to be immunosuppressive and are, as a group, known as soluble inhibitors of the immune system and of immune system function (hereinafter referred to as "soluble inhibitors"). The following non-exhaustive list are known members of the class of soluble inhibitors of the immune system: gangliosides; all known growth factors, most notably TNF-alpha, TGF-beta and variants, PDGF, EGF, IGF and variants, FGF and variants and VEGF; all known inflammatory cytokine receptors most notably the TNF-alpha family—TNF-R1, TNF-R2, CD40L, NGFR, TRAIL and variants, FASL, IL-1R1, IL1R2, IL-2R, IL-3R, IL-5R, IL-6R, IL-7R, GM-CSFR, IL-9R, IL-12R, and erythropoietin receptor. Many patients and most cancer patients have elevated levels of one or more soluble inhibitors which compromise their immune system and inhibit the body from controlling pathogens including bacteria, viruses and cancers.

U.S. Pat. No. 6,156,305 ('305 patent) which is incorporated herein by reference discloses a method of preventing and treating cancer by implanting cancer cells into mammals with a single chamber implant device. The tumor cells can be the patient's own tumor cells or processed tumor cells that contain antigens present in the patient's tumor cells. The boundary of the implant prevents cell to cell contact between the patient's immune system and the tumor cells but allows sub-cellular materials to pass through the chamber. The '305 patent claims a 60% remission rate in tumor bearing experimental animals.

SUMMARY OF THE INVENTION

Briefly, in accordance with the present invention, a mammal is treated with an implant device to elicit an immune response to an antigen wherein the antigen is presented to the mammal's immune system in a protected space in vivo. The mammal is provided with an implant device that contains a protective space for antigen presentation to immune cells, such as dendritic cells, wherein the protective space is surrounded by a soluble inhibitor adsorbent. One or more antigens, or cells containing one or more antigens, are placed into the innermost portion of the protective space of the implant device. A monocyte-containing blood sample obtained from the mammal and one or more dendritic cell inducing factors are also placed into the protective space of the implant device to induce formation of activated dendritic cells from the monocytes. The loaded implant device is implanted into the mammal allowing an immune response to proceed within the protective space which is substantially free of soluble inhibitors. After activated dendritic cells are formed, they are allowed to release from the implant and circulate throughout the mammal's vascular system. The soluble inhibitor adsorbent binds soluble inhibitors and allows antigen presentation to the induced dendritic cells to proceed to completion. The antigen can be any antigen such as bacterial antigens, viral antigens and antigens associated with cancer cells.

In a broad aspect, the present invention creates an immunologically protected/enhanced space in vivo in a mammal by removing the impact of soluble inhibitors of the mammal's immune system in a defined space within the body. Placing an antigen source within the defined protected space along with a monocyte-containing blood sample from the mammal being treated and a dendritic cell inducing factor allows a dendritic-antigen presentation process to proceed to completion. The protected/enhanced space is created by surrounding the protected space with ligands that absorb and/or bind to one or more soluble inhibitors.

In one embodiment, the medical implant device of the present invention contains (a) a biocompatible outer case; (h) an immunologically protected/enhanced inner space that contains (i) one or more antigens, (ii) one or more dendritic cell inducing factors, (iii) a monocyte containing blood sample, such as a buffy coat sample, from a mammal who is the intended recipient of the medical implant device, and (iv) an adsorbent that binds soluble immune inhibitors to a mammalian immune system; and (c) a plug that allows the activated dendritic cells formed in the immunologically protected/enhanced inner space to be released into the mammal's vascular system after the dendritic cell-antigen presentation process proceeded sufficiently to form activated dendritic cells within the immunologically protected inner space.

The configuration of the soluble inhibitor adsorbent defines the immunologically protected inner space. The size of the implant is not critical to the practice of the present invention and the implant can be from several centimeters in length that can be implanted using a minor surgical incision to a miniaturized pellet that can be inserted with, for example, a 12 or 16 gauge needle and syringe.

Alternatively, the medical implant device for mammals contains a biocompatible outer case that allows flow of blood/plasma into the implant device when implanted into a mammal and an immunologically protected inner space that contains (i) one or more antigens, (ii) a leukocyte attractant, and (iii) an adsorbent of soluble immune inhibitors to a mammalian immune system whereby a dendritic cell antigen presentation process is able to proceed sufficiently to form mature activated dendritic cells.

In another aspect, the present invention relates to a medical implant device used to treat cancer in a mammal wherein the implant contains (a) a porous outer biocompatible case, (b) a peripheral region within the biocompatible case that contains ligands that bind to soluble inhibitors of a mammalian immune system and (c) an inner region that contains cancer cell antigens, one or more dendritic cell inducing factors and a leukocyte (buffy coat sample) sample from the mammal to the treated for cancer. The inner region is defined by the configuration of the soluble inhibitor ligands in the peripheral region and provides a protected space in vivo that allows antigen presentation to dendritic cells formed in the inner region from the monocytes contained in the buffy coat sample. A biodegradable plug allows the activated dendritic cells of the inner region to be released into the mammal's vascular system. The biodegradable plug can be designed to degrade over any amount of time such as between about 3 and about 20 days and preferably between about 5 and 7 days. The peripheral region and the inner region are separated by a membrane that is porous to sub-cellular components such as antigenic proteins, inactivated viruses, cytokines, cytokine receptors and the like.

In a further aspect of the present invention, a subcutaneous implant is provided to facilitate the induction of a natural cancer vaccine. It does so by taking an approach never tried before. The device creates an idealized immunologic space in which the natural process of creating a vaccine is protected from the cancer compromised/impacted immune system of the patient. The patient's own blood cells or a fraction thereof are harvested and placed within the implant of the present invention. Another chamber within the device is loaded with cancer cells, preferably harvested from the patient's cancer/tumor, and other substances that will show the cancer to the immune system. A trivial surgical procedure places the implant subcutaneously, to use the patient's own body as an incubator. Alternatively, the implants can be miniaturized into pellet form and injected with a needle and syringe. Within the implant, the vaccine process runs its course. At a pre-determined time, the implant yields a precious cargo of immune cells to the body, and a vaccine against the cancer, is released from the implant. The released immune cells travel to the nearest lymph nodes, where the vaccine will be amplified and propagated throughout the body as antigen presenting cells to T-cells and B-cells.

Of particular interest in practicing the present invention, human patients are treated with the present medical implant device to treat cancer. The patient is provided with an implant device that contains a protective space for antigen presentation to the patient's immune cells, such as dendritic cells, wherein the protective space is surrounded by a soluble inhibitor adsorbent. The protective space is formed by providing ligands which bind or adsorb soluble inhibitors of the patient's immune system preferably positioned around the periphery of the implant device. A sample of the patient's cancer cells is placed into the innermost portion of the protective space of the implant device in a chamber that is porous to sub-cellular components but impervious to cells. A monocyte-containing fraction of the patient's blood such as a buffy coat sample or a leukocyte fraction obtained from the patient and one or more dendritic cell inducing factors are also placed into the protective space but outside the cancer cell-containing chamber to induce formation of activated dendritic cells. Additionally, leukocyte attractants can also be included in the protective space. The loaded implant device is implanted into the patient allowing an immune response to proceed within the protective space, which is substantially free of soluble inhibitors that are bound to the ligands. The immune response includes the presentation of cancer antigens to the activated dendritic cells. After activated dendritic cells are formed and allowed to react with the cancer antigens they are allowed to release from the implant and circulate throughout the mammal's vascular system by the degradation of a biodegradable plug that seals that portion of the medical implant device that contains the monocyte-containing fraction (e.g. buffy coat). The soluble inhibitor adsorbent allows antigen (from the sample cancer cells) presentation to the induced dendritic cells to proceed to completion. After about 9 days or more the implant device is removed and can be replaced with another one. This can be done several times.

In a broad aspect, the present invention creates an immunologically protected/enhanced space in vivo in a mammal by removing the impact of soluble inhibitors of the mammal's immune system in a defined space within the body. Placing an antigen source within the defined protected space along with a leukocyte sample (e.g. buffy coat) from the mammal being treated and one or more dendritic cell inducing factors allows a dendritic-antigen presentation process to proceed to completion in the substantial absence of soluble inhibitors. The protected/enhanced space is created by surrounding the protected space with ligands which absorb and/or bind to one or more soluble inhibitors.

In one embodiment of the present invention, the implant device is made up of three concentric biocompatible hollow fiber membranes, approximately 5 cm long with an outside diameter of about 5-20 millimeters and which can be implanted with a small incision. In another embodiment the implant device comprises injectable pellets having a diameter of from about 0.5 mm to about 2 mm and a length of from about 3-10 mm or more and which can be implanted with a needle and syringe. The injectable pellets can also be made with a configuration of 3 concentric hollow fiber membranes.

The exact size and shape of the implant device is not critical to the practice of the present invention. The outermost portion of the device can be packed with beads that absorb particular chemical messengers that interfere with the immune system, i.e. soluble inhibitors, and defines the protective space within the device. The middle portion or protective space can contain (a) the patient's own immune cells, e.g., buffy coat, (b) dendritic cell growth factors and (c) cancer cells or cancer markers (antigens) wherein the cancer cells or antigens are contained within a separate compartment that is impervious to cells but which is pervious to sub-cellular components. A timed, biodegradable plug degrades over a period of days, eventually breaking down fully, and letting the activated immune cells in the protective space escape into the patient's vascular system to deliver the vaccine into the patient's blood stream.

The various medical implant devices and associated methods of the present invention create an immunologically protected/enhanced space in vivo by removing the impact of soluble inhibitors of the immune system. The process of antigen presentation by induced dendritic cells proceeds to completion in the immunologically protected/enhanced space for the purposes of combating infection, inducing antitumor vaccination or dampening autoimmunity, in-vivo.

DETAILED DESCRIPTION OF THE INVENTION

Figure 1:
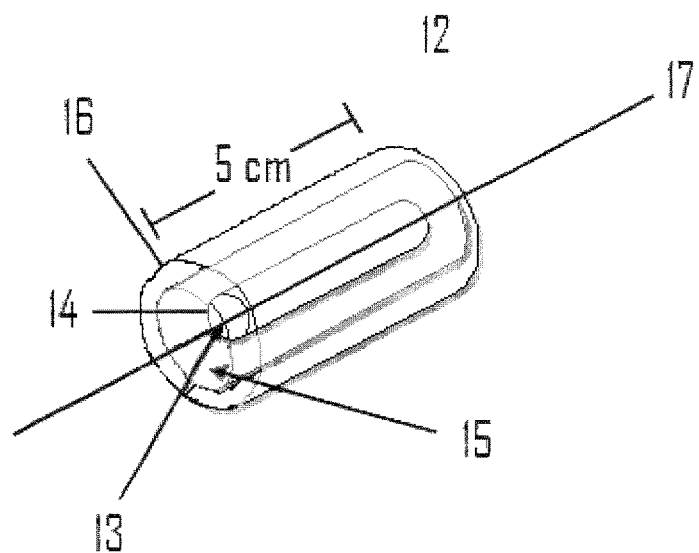
FIG. 1 shows a medical implant device that is implanted into a mammal with a small surgical incision.

In practicing the present invention, a mammal is treated with an implant device to elicit an immune response to an antigen wherein the antigen is presented to the mammal's immune system in vivo. The mammal can be any mammal but humans, non-human primates, dogs, cats, horses, zoo animals, prized breeding bulls and any other commercially valuable agricultural animals are preferred. Any description herein relating to humans is equally applicable to other mammals.

The following definitions apply to the practice of the present invention:

The term "leukocyte fraction" or "leukocyte-containing fraction" refers to any fraction of a mammal's blood that contains white blood cells including monocytes. A buffy coat is a leukocyte fraction.

The term "buffy coat" means" the fraction of an anticoagulated blood sample after density gradient centrifugation that contains most of the white blood cells and platelets.

As used herein the terms "cancer" and "tumor" refer to malignancies including solid tumors, metastatic tumor cells and non-solid cancers of the blood, marrow, and lymphatic systems. "Cancer" and "tumor" shall include: carcinomas (cancers derived from epithelial cells), sarcomas (derived from mesenchymal tissues) lymphomas (solid tumors of lymphoid tissues) and leukemias (marrow or blood borne tumors of lymphocytes or other hematopoietic cells). Specific cancers include bladder cancers, breast cancers, melanomas, lung cancers, renal cancers, endometrial cancers, colon and rectal cancers, brain cancers, thyroid cancers, pancreatic cancers, prostate cancers, non-Hodgkin lymphomas, non-melanoma skin cancers (including basal cell and squamous cell cancers) and leukemias.

The mammal is provided with an implant device that contains a protective space for antigen presentation to immune cells, such as dendritic cells, wherein the protective space is surrounded by a soluble inhibitor adsorbent. One or more antigens, or cells containing one or more antigens, are placed into the innermost portion or chamber of the protective space of the implant device. This innermost chamber contains the antigens or antigenic cells within the innermost portion of the protective space and prevents cellular contact with other cells in the protective space and release of cells into the host mammal. However, the walls of the chamber are pervious to sub-cellular components contained within the protective space. A monocyte-containing blood sample, such as a buffy coat sample, obtained from the mammal to be treated and one or more dendritic cell inducing factors are also placed into the protective space of the implant device to induce formation of mature dendritic cells. The antigens within the protective space are presented to the maturing dendritic cells. The loaded implant device is implanted into the mammal allowing an immune response to proceed within the protective space, which is substantially free of the soluble inhibitors that are adsorbed by the specific ligands contained in the soluble inhibitor adsorbent which surrounds the protective space. After activated dendritic cells are formed in the protective space they are allowed to release from the implant and circulate throughout the mammal's vascular system. The soluble inhibitor adsorbent allows antigen presentation to the induced, maturing dendritic cells to proceed to completion. The antigen can be any antigen such as bacterial antigens, viral antigens and antigens associated with cancer cells or autoimmune disease. The antigens can be any source of antigens including but not limited to recombinant antigenic determinants, inactivated viruses, inactivated virus particles, bacterial cells, and cancer cells. While the exact amount of antigen is not critical to the practice of the present invention usually at least about 0.05 mcg of antigen is employed and preferably 0.1 mcg or more cancer cells are added to the inner most portion of the implant device.

The implant device of the present invention can be made with biocompatible polymers, biopolymers or composite material porous membranes employing manufacturing procedures well known to one of ordinary skill in the art. Polymer membranes having a pore size of from about 0.6 to about 60 µm or more are advantageous. Preferably, the inner membranes (described below) have a pore size less than about 1 µm and the outer membrane (described below) less than about 5 µm. The outermost membrane should promote vascularization around the outside of the implant and membranes having a pore size of about 60 µm are preferred for the purpose of promoting vascularization. All of the membranes should allow sub-cellular components to move freely through the membrane. Suitable polymer membranes include mixed esters of cellulose having a nominal pore size ranging from 1.2 to 8.0 µm; cellulose acetate having a nominal pore size ranging from 0.8 to 8.0 µm; and PTFE/polyester having a nominal pore size ranging from 1.0 to 15 µm. See U.S. Pat. No. 5,964,804, which is incorporated herein by reference.

The biodegradable plug used to release the activated dendritic cells into the patient's circulation according to the present invention may be made of any biodegradable, biocompatible polymer. Biodegradable polymers that are biocompatible are well known to one of ordinary skill in the art. Preferred polymers are selected from the group consisting of a polylactide, polyglycolide, poly(dioxanone), poly(trimethylene carbonate copolymers, poly (ε-caprolactone) homopolymers and copolymers, polyorthoesters, polyphosphazenes, copolymers of polylactide and polyglycolide, copolymers of lactide and lactone, polysaccharides, polyanhydrides, polystyrenes, polyalkylcyanoacrylates, polyamides, poly(methylmethacrylate), polyurethanes, copolymers of methacrylic acid and acrylic acid, copolymers of hydroxyethylmethacrylate and methylmethacrylate, polyaminoacids and polypeptides. Preferred biodegradable, biocompatible polymers for use as the biodegradable plug include polymers from all major suppliers, e.g. PURASORB® of Purac Biomaterials, RESOMER® of Boehringer Ingelheim as well as those supplied by Lakeshore and Lactel/Durect.

Factors that accelerate the degradation time of the polymer include such things as having a more hydrophilic backbone, having more hydrophilic end groups, having more hydrolytic groups in the backbone, having less crystallinity, having more porosity and modification of the mechanical or physical attributes of the polymer plug such as the thickness of the plug. One of ordinary skill in the art can take these considerations into account to optimize the degradation time of the polymer plug without undue experimentation.

In a preferred embodiment of the present invention a biodegradable plug forms the end of the medical implant device adjacent to the portion of the device where the activated immune cells are formed. The degradation of the plug allows the activated immune cells to be released into the patient's circulatory system ultimately ending up in the lymph nodes. For example, the biodegradable plug will form the end of the inner chamber 32 shown in FIG. 3, the outer chamber/compartment 42 shown in FIG. 4 and the outer chamber/compartment 52 shown in FIG. 5. The biodegradable plug is attached to the end of the medical implant device employing standard manufacturing techniques. The chambers containing the patient's monocyte blood fraction, e.g., buffy coat, are loaded by injecting the buffy coat through the biodegradable plug into the chamber.

The innermost chamber of the medical implant device that contains the antigens (e.g. cancer cells) preferably contains a diaphragm through which the antigens are injected into the antigen-containing chamber. When cells are employed as the antigen source the cells are injected into this chamber and contained therein. The diaphragm prevents escape of the cells into the patient's circulatory system. For example the diaphragm will form the end of the innermost chamber 31 shown in FIG. 3, inner antigen chamber/compartment 41 shown in FIG. 4 and the inner antigen chamber/compartment 51 shown in FIG. 5. The diaphragm is attached to the end of the medical implant device employing standard manufacturing techniques. The chambers containing the antigen, e.g. cancer cells, are loaded by injecting the antigen/cells through the diaphragm and into the chamber.

A preferred configuration of the present medical implant device has three concentric hollow fiber membranes having (a) antigens contained in the innermost hollow fiber space, (b) the patient's monocytes and one or more dendritic cell growth factors in the middle hollow fiber space, and (c) a soluble inhibitor adsorbent in the outermost hollow fiber space. The soluble inhibitor adsorbent can be a matrix comprised of beads that contain ligands that bind soluble inhibitors of the patient's immune system thereby providing the protective space within the medical implant device that allows the antigen(s) of the patient's cancer cells to fully react with the patient's immune system, e.g., activate dendritic cells. Monocytes are typically provided with a leukocyte fraction or buffy coat sample obtained from the mammal to be treated.

Antigens that are present in the present implant can be any antigens to which an appropriate immune response by the patient is desired. Antigens include bacterial antigens, viral antigens, tumor antigens and any antigens present in cancer cells. Antigens can be recombinant antigenic domains, purified antigenic proteins or cells that contain/express antigens. When the present implant device is used to treat cancer the antigens can be autologous cancer cells or allogenic cancer cells having antigens in common with the patient's cancer. Allogenic cancer cells can be surgically removed from another patient or can be taken from an in vitro cancer cell line. Preferably, the antigens used in the present medical implant device are autologous cancer cells harvested from the treated patient's own tumor using well known surgical techniques.

The antigens are placed in an inner compartment (antigen compartment) of the implant device wherein the compartment wall is porous to sub-cellular components but impervious to cells. It is important that bacteria and cancer cells are contained within the inner compartment and not released into the blood stream of the mammal being treated. Bacteria cells or cancer cells are harvested and placed into the inner antigen compartment, which is then sealed to prevent release of the cells into the mammal's blood stream. Alternatively, the present implant device is made having a diaphragm that allows antigens, preferably cancer cells, to be injected directly into the inner, antigen-containing compartment.

In a preferred embodiment, cancer cells are harvested from a cancer patient by a surgical procedure or a needle biopsy and, placed into the inner antigen compartment which is then sealed, or injected directly into the inner antigen compartment through a diaphragm.

Optionally, abrasive materials can be added to the inner antigen compartment when the inner antigen compartment contains cells. The abrasive materials will control overgrowth of cells in the inner antigen compartment when implanted into a mammal. The abrasive materials mechanically disrupt cell wall membranes and will control overgrowth of bacterial or cancer cells contained within the inner antigen compartment while the implant is implanted within a mammals' body. The abrasive material can be abrasive heads or abrasive fibers. Abrasive heads can be coated with abrasive inorganic compounds. Suitable abrasive fibers include silicon fiber whiskers and ceramic whiskers.

In a preferred embodiment, dendritic cell inducing factors are present in the present medical device within the protective space. These factors can be present in any form that reacts with the patient's monocytes to form dendritic cells. The dendritic cell inducing factors can be bound to polymer beads or imbued into porous polymer beads where they can diffuse into the protective space. The beads can be any commercially available chromatographic column bead such as Pierce Ultra Link beads. The size of the heads is not critical to the practice of the present invention and are typically 50-100 μm in diameter. Suitable beads include a highly cross linked his-acrylamide/azolactone copolymer head. Preferably, the dendritic cell inducing factors are covalently bound to the polymer membranes present in the medical device employing standard manufacturing procedures well known to one of ordinary skill in the art. Dendritic cell inducing factors that are bound/imbued to the heads or bound to a membrane include IL-4, GM-CSF, IL-10, IL-13, the IL-17 family of cytokines and the IL-18 family of cytokines. The dendritic cell inducing factors are placed into the protective space of the present implant device with the buffy coat or leukocyte fraction that contains monocytes or bound to an appropriate membrane that is in contact with the monocytes present in the device.

Soluble inhibitors of the immune system are well known and include gangliosides; all known growth factors, most notably TNF-alpha, TGF-beta and variants, PDGF, EGF, IGF and variants, FGF and variants and VEGF; all known inflammatory cytokine receptors, most notably the TNF-alpha family—TNF-R1, TNF-R2, CD40L, NGFR, TRAIL and variants, FASL, IL-1R1, IL1R2, IL-2R, IL-3R, IL-5R, IL-6R, IL-7R, GM-CSFR, IL-9R, IL-12R, and erythropoietin receptor. Ligands which that to one or more of the soluble inhibitors are bound to a solid support and configured in the present implant to define the protective space within the implant. The ligands of the soluble inhibitors are bound to polymer beads such as those used to deliver the dendritic cell-inducing factors described herein. Preferably, the ligands are covalently hound to the polymer membranes present in the medical device employing standard manufacturing procedures well known to one of ordinary skill in the art. The membrane in which the ligands are bound should be a membrane outside the inner most membrane that contains the antigens. Preferred ligands include those that bind to TGF-beta, TNF-R1 and TNF-R2.

The implant can be inserted into any subcutaneous tissue in the body. Suitable locations include the inner aspect of an arm, the lateral midline area of the chest below the arm pit, a side region of the abdomen and the inner aspect of the thigh. It is preferred to place the implant as far away as possible from the site of the primary tumor and any metastatic lesion. The implant insertion can conveniently be done as a minor surgical procedure in an outpatient facility. After the biodegradable plug has degraded the implant is then removed. Additional implants can be administered in different body locations as deemed necessary by a healthcare practitioner. As one implant is removed a new implant can be administered. Alternatively, additional implants can be spaced out at one or two week intervals. In another embodiment, two or more implants can be implanted at the same time. The patient's cancer is monitored using standard diagnostic/monitoring techniques such as blood testing to determine cancer marker levels, X-rays and scans.

The medical implant device of the present invention can be administered to a patient at any time but it is preferred to administer the implant when the patient's immune system is not in a compromised condition such as during and shortly after the administration of chemotherapy or radiation treatments. Once the patient's white blood cell count is within normal ranges, then the present implant is preferably administered. Other lifestyle choices to bolster the patient's immune system are of benefit. These lifestyle choices include plenty of sleep, moderate exercise, an insulin lowering diet, consumption of EPA and DHA as well as other omega-3 fatty acids such as those found in cold water ocean fish (salmon, tuna, sardines, mackerel, etc), a reduction in omega-6 fatty acids, elimination of trans-fats from the diet, restricted ingestion of alpha linolenic acid and the like. Immune enhancing supplements, such as Vit C, co-enzyme Q-10 and Vit D, can also be taken.

In a preferred embodiment of the present invention, the loaded implant is placed into the patient by inserting it into a small incision made at a desirable location or by injecting implant pellets with a needle and syringe. The implant is preferably left in the patient's body until at least after the biodegradable plug has degraded and supplied the activated immune cells into the patient's vascular system. Another implant can then be implanted and repeated as many times as desired depending on the patient's response.

FIG. 1 is a drawing illustrating one embodiment of the medical implant device of the present invention 12. Line 17 represents an axis through the middle of the medical implant device. Three concentric hollow fibers approximately 50 millimeters long are loaded as follows: Innermost hollow fiber 13 is filled with tumor cells or tumor antigen in plasma (or other vehicle) and is sealed at the end 14 so that no tumor cells can escape from the innermost hollow fiber. The middle (second innermost section) hollow fiber 15 is filled with a mixture of cells from the patient's blood commonly referred to as the "buffy coat," which comprises macrophages, T-cells, B-cells, and other leukocytes. The middle hollow fiber also contains 20-100 micron beads imbued with dendritic cell inducing factors including one or more of the following: IL-4, GM-CSF, IL-10, IL-13 and TNF-alpha with or without members of the IL-17 or IL-18 families of cytokines. The middle hollow fiber is also equipped with a biodegradable polymer plug (not shown) which allows activated immune cells to be released from the middle hollow fiber into the patient's vascular system when the plug degrades in 5-7 or more days. The outer (outermost section) hollow fiber 16 is packed with 20-100 micron beads saturated with bound ligand for the purposes of adsorbing and acting as a concentration sink for soluble inhibitors of the immune system. The outer hollow fiber is sealed to prevent escape of beads into the patient's vascular system.

The described medical device implant, which has an outside diameter of about 5 mm, is implanted into a patient with a minor surgical incision and forcefully shields the antigen presentation process from soluble inhibitors of the immune system, facilitating an immune response overcoming inhibitor-induced anergy. The immune response is also triggered by the presence of highly localized concentrations of dendritic cell inducing cytokines and T-cell activation factors while simultaneously exposing the leukocyte fraction to the antigens of interest diffusing from the center hollow fiber.

Figure 2:
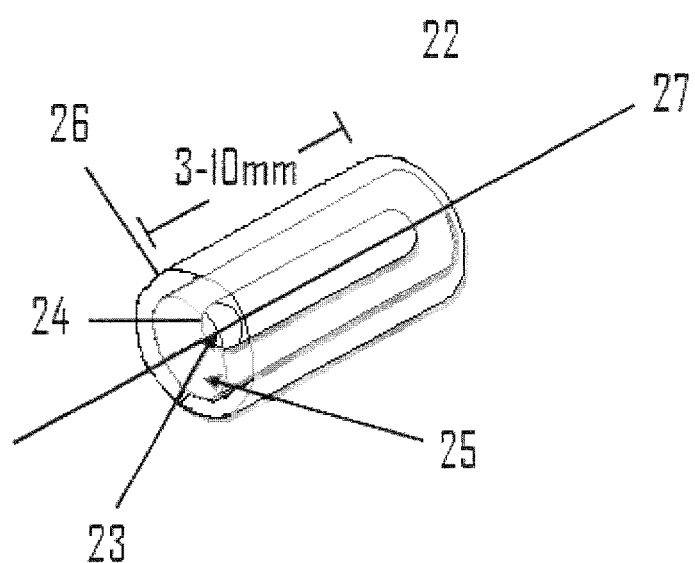
FIG. 2 shows a medical implant device pellet that is implanted into a mammal with a needle and syringe.

FIG. 2 is a drawing illustrating another embodiment of the medical device of the present invention as an injectable pellet implant 22. Line 27 represents an axis through the middle of the medical implant device. Three concentric hollow fibers approximately 5 millimeters long are loaded as follows: Innermost hollow fiber 23 is filled with tumor cells or tumor antigen in plasma (or other vehicle) and is sealed at the end 24 so that no tumor cells can escape from the innermost hollow fiber. The middle hollow fiber 25 is filled with a mixture of cells from the patient's blood commonly referred to as the "buffy coat," which comprises monocytes, macrophages, T-cells, B-cells, and other leukocytes. The middle hollow fiber also contains 20-100 micron beads (not shown) imbued with dendritic cell inducing factors including one or more of the following: IL-4, GM-CSF, IL-10, IL-13 and TNF-alpha with or without members of the IL-17 or IL-18 families of cytokines. The middle hollow fiber is also equipped with a biodegradable polymer plug (not shown) which allows activated immune cells to be released from the middle hollow fiber into the patient's vascular system when the plug degrades in 5-9 or more days. The outer hollow fiber 26 is packed with 20-100 micron beads saturated with bound ligand for the purposes of adsorbing and acting as a concentration sink for soluble inhibitors of the immune system. The outer hollow fiber is sealed to prevent escape of beads into the patient's vascular system. The described medical device implant, having an outside diameter of about 1-2 mm, is implanted into a patient with a needle and syringe (12-16 gauge needles) and forcefully shields the antigen presentation process from soluble inhibitors of the immune system, facilitating an immune response overcoming inhibitor-induced anergy. The immune response is also triggered by the presence of highly localized concentrations of dendritic cell inducing cytokines and T-cell activation factors while simultaneously exposing the leukocyte fraction to the antigens of interest diffusing from the center hollow fiber.

Figure 3:
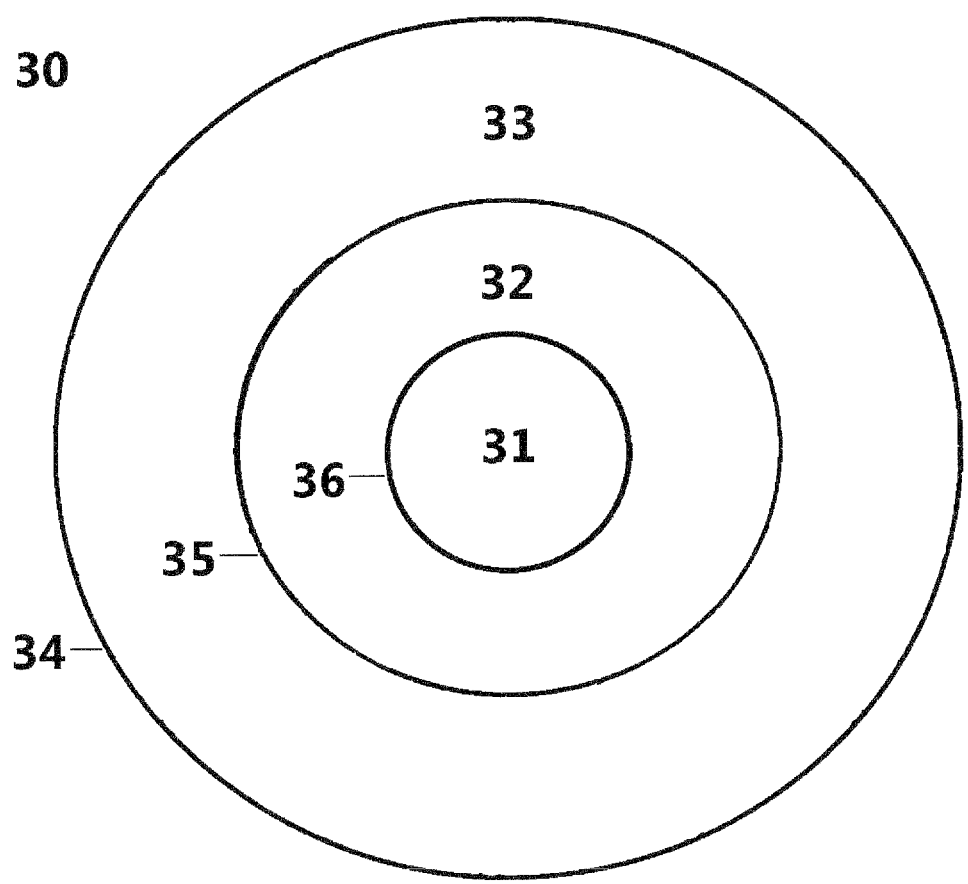
FIG. 3 is a cross-sectional view of a medical implant device of the present invention configured as three concentric hollow fiber membranes.

FIG. 3 is a drawing that shows a cross-sectional view of an implant of the present invention 30 used to treat cancer and is made of 3 concentric hollow fiber membranes 34, 35 and 36. The innermost hollow fiber membrane 36 defines the innermost chamber 31 which contains cancer cells (not shown) from the patient to be treated. Hollow fiber membrane 36 is impervious to cells but pervious to sub-cellular components such as antigens, cytokines, cytokine receptors, and the like. Hollow fiber membrane 36 is sealed at both ends to prevent cancer cells (not shown) from being released into the patient's vascular system. The middle hollow fiber membrane 35 defines the middle chamber 32 which contains a buffy coat sample (not shown) from the patient to be treated along with one or more dendritic cell-inducing factors (not shown). Hollow fiber membrane 35 is impervious to cells but pervious to sub-cellular components such as antigens, cytokines, cytokine receptors, and the like. Hollow fiber membrane 35 is sealed at one end and on the other end is sealed with a biodegradable polymer plug (not shown) which will degrade over time and allow the patient's immune cells and other sub-cellular components contained therein to be released into the patient's vascular system. The outermost hollow fiber membrane 34 defines the outermost chamber 33 which contains a matrix having ligands that bind to soluble inhibitors of the immune system (not shown). Such ligands are typically bound to inert polymer beads. Hollow fiber membrane 34 is impervious to cells but pervious to sub-cellular components such as antigens, cytokines, cytokine receptors, and the like and also promotes vascularization and inhibits encapsulation by the patient's immune system. Hollow fiber membrane 34 is sealed at both ends (not shown) to prevent the soluble inhibitor matrix from being released into the patient's vascular system. Soluble inhibitors which circulate throughout the cancer patient's vascular system can enter the medical implant device but are adsorbed onto the ligands contained in the outermost portion 33 of the implant device 30 which provides the protected space in the middle portion 32 and innermost portion 31 of medical implant device 30.

Figure 4:
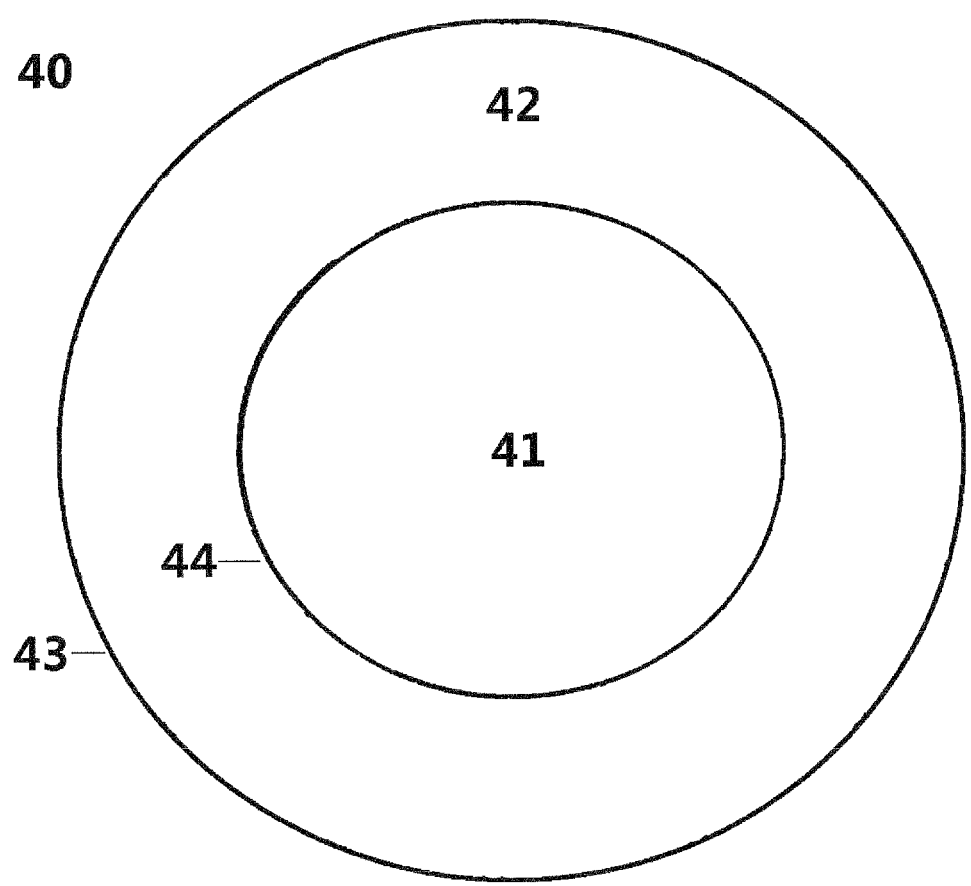
FIG. 4 is a cross sectional view of a medical implant device of the present invention configured as two concentric hollow fiber membranes.

FIG. 4 is a drawing that shows a cross-sectional view of an implant of the present invention 40 used to treat cancer and is made of 2 concentric hollow fiber membranes 43 and 44. The innermost hollow fiber membrane 43 defines an inner antigen chamber or compartment 41 which contains cancer cells (not shown) from the patient to be treated. Hollow fiber membrane 43 is impervious to cells but pervious to sub-cellular components such as antigens, cytokines, cytokine receptors, and the like. Hollow fiber membrane 43 is sealed at both ends to prevent cancer cells (not shown) from being released into the patient's vascular system. The outer hollow fiber membrane 44 defines the outer chamber or compartment 42 which contains a buffy coat sample (not shown) from the patient to the treated along with (a) one or more dendritic cell inducing factors (not shown) and (b) one of more soluble inhibitor ligands (not shown). The outer hollow fiber membrane 44 is impervious to cells but pervious to sub-cellular components such as antigens, cytokines, cytokine receptors, and the like. Hollow fiber membrane 44 is sealed at one end and on the other end is sealed with a biodegradable polymer plug (not shown) which will degrade over time and allow the patient's immune cells and other sub-cellular components contained therein to be released into the patient's vascular system. Hollow fiber membrane 44 also promotes vascularization and inhibits encapsulation by the patient's immune system. Soluble inhibitors which circulate throughout the cancer patient's vascular system can enter the medical implant device but are adsorbed onto the ligands contained in the outer chamber or compartment 42 of the implant device 40 which provides a protected space in both the inner chamber or compartment 41 and the outer chamber 42 of medical implant device 40.

Figure 5:
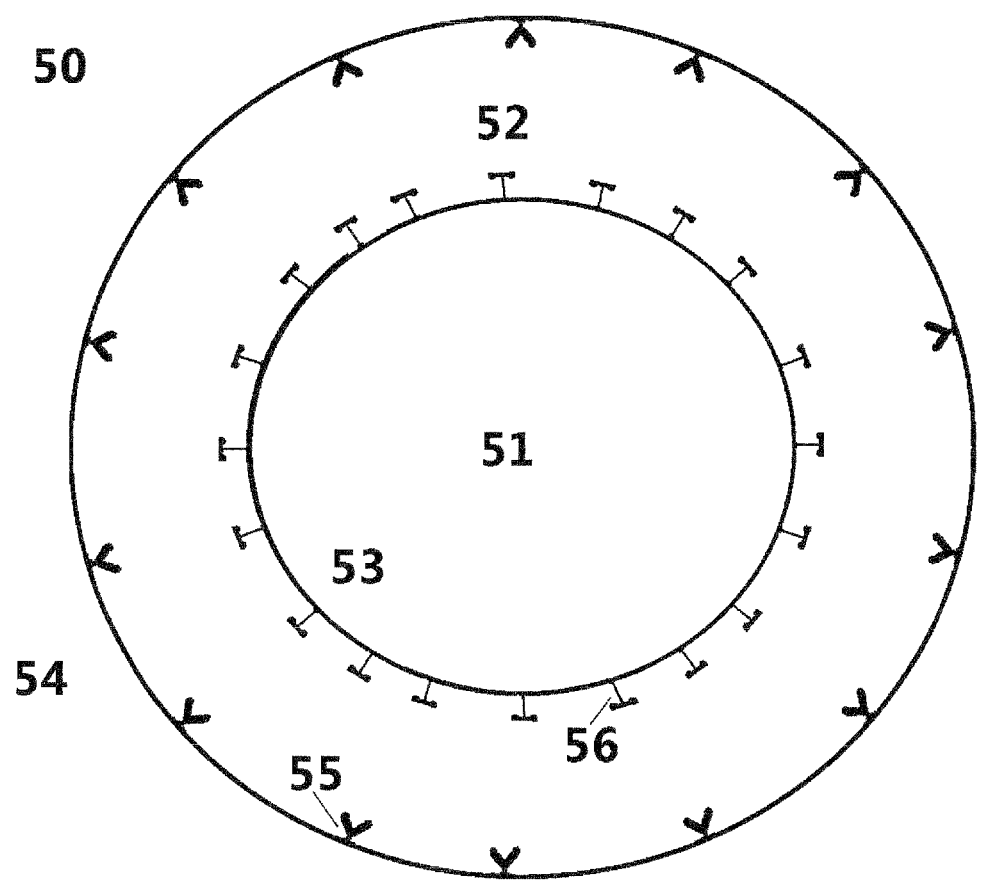
FIG. 5 is a cross sectional view of a medical implant device of the present invention configured as two cross sectional hollow fiber membranes wherein ligands of soluble inhibitors and dendritic cell growth factors are covalently bound to the hollow fiber membranes.

The ligands of soluble inhibitors and the dendritic cell inducing factors can be bound to polymer beads as described herein or they can be covalently bound to the hollow fiber membranes 43 and 44 as shown in FIG. 5.

FIG. 5 is a drawing that shows a cross-sectional view of an implant of the present invention 50 used to treat cancer and is made of 2 concentric hollow fiber membranes 53 and 54. The innermost hollow fiber membrane 53 defines an inner antigen chamber or compartment 51 which contains cancer cells (not shown) from the patient to be treated. The outer hollow fiber membrane 54 defines the outer chamber or compartment 52 which contains a leukocyte-containing blood sample, such as a buffy coat sample, (not shown) from the patient to be treated. The outer hollow fiber membrane 54 is impervious to cells but pervious to sub-cellular components such as antigens, cytokines, cytokine receptors, and the like. Hollow fiber membrane 54 is sealed at one end and on the other end is sealed with a biodegradable polymer plug (not shown) which will degrade over time and allow the patient's immune cells and other sub-cellular components contained in compartment 52 to be released into the patient's vascular system. Hollow fiber membrane 54 also promotes vascularization and inhibits encapsulation by the patient's immune system. Hollow fiber membrane 53 is impervious to cells but pervious to sub-cellular components such as antigens, cytokines, cytokine receptors, and the like. Ligands of soluble inhibitors of the immune system 56 (shown as "Y") are covalently bound to the hollow fiber membrane 54 and dendritic cell growth factors 55 (shown as "T") are covalently bound to hollow fiber membrane 53 employing standard manufacturing techniques well know to one of ordinary skill in the art. In an alternative embodiment the ligands of soluble inhibitors may be attached to the inner hollow fiber membrane 53 and the dendritic cell growth factors may be attached to the outermost hollow fiber membrane 54. In a further embodiment, both the soluble inhibitor ligands and dendritic cell growth factors can be attached to both hollow fiber membranes 53 and 54. Hollow fiber membrane 43 is sealed at both ends to prevent cancer cells (not shown) from being released into the patient's vascular system.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A method of creating antigen exposed dendritic cells within an immunologically protected/enhanced space in vivo in a mammal which comprises:
   a) removing the impact of soluble inhibitors of the mammal's immune system in a defined space within the mammal's body;
   b) placing dendritic cells, dendritic cell precursors, or monocytes within the defined space; and
   c) placing an antigen source within the defined space to allow a dendritic-antigen presentation process to proceed; and
   wherein the defined space is created by providing one or more ligands that bind to soluble inhibitors of the mammal's immune system.

2. The method of claim 1 wherein the antigen source is one or more bacterial antigens, one or more viral antigens or one or more cancer cell antigens.

3. The method of claim 2 wherein the mammal has a cancer and the one or more cancer antigens are autologous cancer cells harvested from the mammal's cancer.

4. The method of claim 1, wherein the ligands bind with one or more of the soluble inhibitors of the immune system selected from the group consisting of gangliosides, growth factors, TNF-alpha, TGF-beta and variants thereof, PDGF, EGF, IGF and variants thereof, FGF and variants thereof, VEGF, inflammatory cytokine receptors selected from the group consisting of the TNF-alpha family: TNF-R1, TNF-R2, CD40L, NGFR, TRAIL and variants, FASL, IL-1R1, IL1R2, IL-2R, IL-3R, IL-5R, IL-6R, IL-7R, GM-CSFR, IL-9R, IL-12R, and erythropoietin receptor.

5. The method of claim 1, wherein the mammal is a human.

6. The method according to claim 1, which comprises:
   a) providing an enclosed space within the mammal, said enclosed space comprising an internal region and a peripheral region wherein the peripheral region contains ligands that bind soluble inhibitors of the mammalian immune system;
   b) placing within the internal region of the enclosed space:
      (i) one or more antigens or cells containing one or more antigens,
      (ii) a fraction of the mammal's blood that contains dendritic precursor cells, and
      (iii) one or more dendritic cell inducing factors;
   c) allowing dendritic cells to be induced whereby antigen presentation to said induced dendritic cells proceeds in the substantial absence of soluble inhibitors of the mammal's immune system to form activated dendritic cells; and
   d) releasing the activated dendritic cells to circulate through the mammal's vascular and/or immune system.

7. The method of claim 6 wherein the one or more antigens are one or more bacterial antigens, one or more viral antigens or one or more cancer cell antigens.

8. The method of claim 7 wherein the mammal has a cancer and the one or more cancer antigens are autologous cancer cells harvested from the mammal's cancer.

9. The method of claim 8 wherein the ligands bind with one or more of the soluble inhibitors of the immune system selected from the group consisting of gangliosides, growth factors, TGF-alpha, TGF-beta and variants thereof, PDGF, EGF, IGF and variants thereof, FGF and variants thereof, VEGF, inflammatory cytokine receptors TNF-alpha family:
   TNF-R1, TNF-R2, CD40L, NGFR, TRAIL and variants, FASL, IL-1R1, IL1R2, IL-3R, IL-5R, IL-6R, IL-7R, GM-CSFR, IL-9R, IL-12R, and erythropoietin receptor.

10. The method of claim 9 wherein the dendritic cell-inducing factors comprise IL-4, GM-CSF, IL-10, IL-13, an IL-17 cytokine, an IL-18 cytokine or mixtures thereof.

11. The method of claim 6 wherein the enclosed space is located in subcutaneous tissue.

12. The method of claim 8 wherein the enclosed space is located in subcutaneous tissue.

13. A method of treating a mammal with cancer wherein said method comprises:
   a) providing an enclosed space within a mammal, said enclosed space comprising an internal region and a peripheral region wherein the peripheral region contains ligands that bind soluble inhibitors of the mammalian immune system and defines the internal region;
   b) placing within the internal region of the enclosed space:
      (i) one or more cancer cell antigens or a sample of the mammal's cancer cells,
      (ii) a fraction of the mammal's blood that contains monocyte cells, and
      (iii) one or more dendritic cell inducing factors;
   c) allowing dendritic cells to be induced from said monocyte cells whereby antigen presentation to said induced dendritic cells proceeds in the substantial absence of soluble inhibitors of the mammal's immune system to form activated dendritic cells; and
   d) releasing the activated dendritic cells into the mammal's vascular and/or immune system.

14. The method of claim 13 wherein the cancer cells are autologous cells harvested from the patient's cancer.

15. The method of claim 13 wherein the cancer cells are placed into a chamber having a chamber wall in the internal region wherein said chamber wall is impervious to cells but porous to sub-cellular components.

16. The method of claim 13 wherein ligands that bind with one or more of the soluble inhibitors of the immune system are one or more ligands selected from the group consisting of gangliosides, growth factors, TGF-alpha, TGF-beta and variants thereof, PDGF, EGF, IGF and variants thereof, FGF and variants thereof, VEGF, inflammatory cytokine receptors selected from the group consisting of TNF-alpha family: TNF-R1, TNF-R2, CD40L, NGFR, TRAIL and variants, FASL, IL-1R1, IL1R2, IL-2R, IL-3R, IL-5R, IL-6R, IL-7R, GM-CSFR, IL-9R, IL-12R, and erythropoietin receptor.

17. The method of claim 13 wherein the dendritic cell inducing factors comprise IL-4, GM-CSF, IL-10, IL-13, an IL-17 cytokine, an IL-18 cytokine or mixtures thereof.

18. A method of treating a mammal that has cancer with an implant device which comprises:
   a) providing an implant device that contains a protective space for antigen presentation to dendritic cells wherein said protective space is surrounded by a soluble inhibitor adsorbent;
   b) placing one or more antigens or cells containing one or more antigens into the protective space of the implant device;
   c) placing a leukocyte fraction of blood obtained from the mammal and one or more dendritic cell inducing factors into the protective space of the implant device to induce formation of dendritic cells to form a loaded implant device;
   d) inserting the loaded implant device into the mammal; and
   e) releasing the induced dendritic cells from the implant into the mammal's vascular and/or immune system,
   whereby the soluble inhibitor adsorbent allows antigen presentation to the induced dendritic cells to proceed.

19. The method of claim 18 wherein the one or more antigens are one or more bacterial antigens, one or more viral antigens or one or more cancer cell antigens.

20. The method of claim 19 wherein the one or more cancer antigens are autologous cancer cells harvested from the mammal's cancer.

21. The method of claim 20 wherein the soluble inhibitor adsorbent comprises one or more ligands that bind with one or more of the soluble inhibitors of the immune system selected from the group consisting of gangliosides, growth factors, TGF-alpha, TGF-beta and variants thereof, PDGF, EGF, IGF and variants thereof, FGF and variants thereof, VEGF, inflammatory cytokine receptors selected from the group consisting of TNF-alpha family: TNF-R1, TNF-R2, CD40L, NGFR, TRAIL and variants, FASL, IL-1R1, IL1R2, IL-3R, IL-5R, IL-6R, IL-7R, GM-CSFR, IL-9R, IL-12R, and erythropoietin receptor.

22. The method of claim 18 wherein the dendritic cell-inducing factors comprise IL-4, GM-CSF, IL-10, IL-13, an IL-17 cytokine, an IL-18 cytokine or mixtures thereof.

23. The method of claim 18 wherein the loaded implant is inserted through an incision in the skin into a subcutaneous tissue.

24. The method of claim 18 wherein the loaded implant is inserted into subcutaneous tissue with a needle and syringe.

25. A method of treating a patient that has cancer with an implant device which comprises:
 a) providing an implant device that contains a protective space for cancer antigen presentation to dendritic cells wherein said protective space is surrounded by a soluble inhibitor adsorbent;
 b) placing one or more cancer antigens or cancer cells into the protective space of the implant device;
 c) placing a leukocyte fraction of a blood sample obtained from the patient and one or more dendritic cell-inducing factors into the protective space of the implant device to induce formation of dendritic cells to form a loaded implant device;
 d) inserting the loaded implant device into the patient; and
 e) releasing the formed dendritic cells from the implant into the patient's vascular and/or immune system;
whereby the soluble inhibitor adsorbent allows antigen presentation to the induced dendritic cells to proceed.

26. The method of claim 25 wherein the cancer cells are autologous cells harvested from the patient's cancer.

27. The method of claim 25 wherein the cancer cells are placed into a chamber having a chamber wall in the protective space wherein said chamber wall is impervious to cells but porous to sub-cellular components.

28. The method of claim 25 wherein the implant device comprises polymeric components that are impervious to cells but porous to sub-cellular components.

29. The method of claim 25 wherein the loaded implant device is inserted through an incision in the skin into subcutaneous tissue.

30. The method of claim 25 wherein the loaded implant device is inserted into subcutaneous tissue with a needle and syringe.

31. The method of claim 25 wherein the soluble inhibitor adsorbent comprises one or more ligands that bind with one or more of the soluble inhibitors of the immune system selected from the group consisting of gangliosides, growth factors, TGF-alpha, TGF-beta and variants thereof, PDGF, EGF, IGF and variants thereof, FGF and variants thereof, VEGF, inflammatory cytokine receptors selected from the group consisting of the TNF-alpha family: TNF-R1, TNF-R2, CD40L, NGFR, TRAIL and variants, FASL, IL-1R1, IL1R2, IL-2R, IL-3R, IL-5R, IL-6R, IL-7R, GM-CSFR, IL-9R,IL-12R, and erythropoietin receptor.

32. The method of claim 25 wherein the dendritic cell inducing factors comprise IL-4, GM-CSF, IL-10, IL-13, an IL-17 cytokine, an IL-18 cytokine or mixtures thereof.

33. A medical implant device for mammals which comprises:
 a) a porous biocompatible outer case and
 b) an immunologically protected/enhanced inner space that contains
  (i) one or more antigens,
  (ii) one or more dendritic cell-inducing factors,
  (iii) a leukocyte fraction of a blood sample from a mammal who is the intended recipient of the medical implant device, and
  (iv) an adsorbent of soluble inhibitors to a mammalian immune system and
 c) a biodegradable plug.

34. The medical implant device of claim 33 wherein the one or more antigens are bacterial antigens, viral antigens or cancer cell antigens.

35. The medical implant device of claim 34 wherein the mammal has a cancer and the one or more antigens are autologous cancer cells harvested from the mammal's cancer.

36. The medical implant device of claim 34 wherein the cancer cells are placed into a chamber in the immunologically protected inner space wherein said chamber is impervious to cells but porous to sub-cellular components.

37. The medical implant device of claim 33 wherein the porous biocompatible outer case comprises polymeric components that are impervious to cells but porous to sub-cellular components.

38. The medical implant device of claim 33 wherein the implant device is configured for administration by insertion through an incision in the skin into subcutaneous tissue.

39. The medical implant device of claim 33 wherein the implant device is configured for administration by insertion into subcutaneous tissue with a needle and syringe.

40. The medical implant device of claim 33 wherein the adsorbent of soluble inhibitors comprises one or more ligands that bind with one or more of the soluble inhibitors of the immune system selected from the group consisting of gangliosides, growth factors, TGF-alpha, TGF-beta and variants thereof, PDGF, EGF, IGF and variants thereof, FGF and variants thereof, VEGF, inflammatory cytokine receptors selected from the group consisting of the TNF-alpha family: TNF-R1, TNF-R2, CD40L, NGFR, TRAIL and variants, FASL, IL-1R1, IL1R2, IL-2R, IL-3R, IL-5R, IL-6R, IL-7R, GM-CSFR, IL-9R, IL-12R, and erythropoietin receptor.

41. The medical implant device of claim 33 wherein the one or more dendritic cell inducing factors are selected from the group consisting of IL-4, GM-CSF, IL-10, IL-13, an IL-17 cytokine and an IL-18 cytokine.

42. A medical implant device to produce an immune response to an antigen in a mammal which comprises:
 a) a porous outer biocompatible case,
 b) a peripheral region within the biocompatible case that contains ligands which bind to soluble inhibitors to a mammalian immune system,
 c) an inner region which contains one or more antigens, a leukocyte fraction of a blood sample from the mammal to be treated and one or more dendritic cell inducing factors and
 d) a biodegradable plug,
wherein the peripheral region and the inner region are separated by a membrane that is porous to cytokines and cytokine receptors but not to cells.

43. The medical implant device of claim 42 wherein the one or more antigens are bacterial antigens, viral antigens or cancer cell antigens.

44. The medical implant device of claim 43 wherein the cancer cell antigens are autologous cancer cells harvested from the mammal to be treated with said medical implant device.

45. The medical implant device of claim 44 wherein the cancer cells are placed into a chamber in the inner region wherein said chamber is impervious to cells but porous to sub-cellular components.

46. The medical implant device of claim 42 wherein the implant device is configured for administration by insertion through an incision into subcutaneous tissue.

47. The medical implant device of claim 42 wherein the implant device is configured for administration by insertion into subcutaneous tissue with a needle and syringe.

48. The medical implant device of claim 42 wherein the ligands bind with one or more of the soluble inhibitors of the immune system selected from the group consisting of gangliosides, growth factors, TGF-alpha, TGF-beta and variants thereof, PDGF, EGF, IGF and variants thereof, FGF and variants thereof, VEGF, inflammatory cytokine receptors selected from the group consisting of the TNF-alpha family: TNF-R1, TNF-R2, CD40L, NGFR, TRAIL and variants, FASL, IL-1R1, IL1R2, IL-2R, IL-3R, IL-5R, IL-6R, IL-7R, GM-CSFR, IL-9R, IL-12R, and erythropoietin receptor.

49. The medical implant device of claim 42 wherein the one or more dendritic cell inducing factors are selected from the group consisting of IL-4, GM-CSF, IL-10, IL-13, an IL-17 cytokine and an IL-18 cytokine.

50. A medical implant device for mammals which comprises:
   a) a biocompatible outer case that allows flow of blood into the implant device when implanted into a mammal and
   b) an immunologically protected inner space which contains
      (i) one or more antigens,
      (ii) dendritic cells and/or monocytes,
      (iii) a leukocyte attractant, and
      (iv) an adsorbent of soluble inhibitors to a mammalian immune system
whereby a dendritic cell-antigen presentation process is able to proceed sufficiently to form activated dendritic cells.

51. The medical implant device of claim 50 wherein the one or more antigens are bacterial antigens, viral antigens or cancer cell antigens.

52. The medical implant device of claim 51 wherein the cancer cell antigens are autologous cancer cells harvested from the mammal to be treated with said medical implant device.

53. Inc medical implant device of claim 52 wherein the cancer cells are placed into a chamber in the immunologically protected inner space wherein said chamber is impervious to cells but porous to sub-cellular components.

54. The medical implant device of claim 50 wherein the implant device is configured for administration by insertion through an incision into subcutaneous tissue.

55. The medical implant device of claim 50 wherein the implant device is configured for administration by insertion into subcutaneous tissue with a needle and syringe.

56. The medical implant device of claim 50 wherein the adsorbent of soluble inhibitors comprises one or more ligands that bind with one or more of the soluble inhibitors of the immune system selected from the group consisting of gangliosides, growth factors, TGF-alpha, TGF-beta and variants thereof, PDGF, EGF, IGF and variants thereof, FGF and variants thereof, VEGF, inflammatory cytokine receptors selected from the group consisting of the TNF-alpha family: TNF-R1, TNF-R2, CD40L, NGFR, TRAIL and variants, FASL, IL-1R1, IL1R2, IL-2R, IL-3R, IL-5R, IL-6R, IL-7R, GM-CSFR, IL-9R, IL-12R, and erythropoietin receptor.

57. A medical implant device to treat cancer in a mammal which comprises:
   a) a porous outer biocompatible case,
   b) a peripheral region within the biocompatible case that contains ligands which bind to soluble inhibitors to a mammalian immune system,
   c) an inner region which contains cancer antigens and a leukocyte fraction of a blood sample from the mammal to be treated for cancer, and
   d) a biodegradable plug
wherein the peripheral region and the inner region are separated by a membrane that is porous to cytokines and cytokine receptors but impervious to cells.

58. The medical implant device of claim 57 wherein the cancer antigens are autologous cancer cells harvested from the mammal's cancer.

59. The medical implant device of claim 58 wherein the cancer cells are placed into a chamber in the inner region wherein said chamber wall is impervious to cells but porous to sub-cellular components.

60. The medical implant device of claim 57 wherein the porous outer biocompatible case comprises polymeric components that are impervious to cells but porous to sub-cellular components.

61. The medical implant device of claim 57 wherein the implant device is configured for administration by insertion through an incision into subcutaneous tissue.

62. The medical implant device of claim 57 wherein the implant device is configured for administration by insertion into subcutaneous tissue with a needle and syringe.

63. The medical implant device of claim 57 wherein the ligands bind with one or more of the soluble inhibitors of the immune system selected from the group consisting of gangliosides, growth factors, TGF-alpha, TGF-beta and variants thereof, PDGF, EGF, IGF and variants thereof, FGF and variants thereof, VEGF, inflammatory cytokine receptors selected from the group consisting of the TNF-alpha family: TNF-R1, TNF-R2, CD40L, NGFR, TRAIL and variants, FASL, IL-1R1, IL1R2, IL-2R, IL-3R, IL-5R, IL-6R, IL-7R, GM-CSFR, IL-9R, IL-12R, and erythropoietin receptor.

64. The medical implant device of claim 57 further comprising one or more dendritic cell inducing factors selected from the group consisting of IL-4, GM-CSF, IL-10, IL-13, an IL-17 cytokine and an IL-18 cytokine.

65. A medical implant pellet to treat cancer in a mammal that can be administered with a needle and syringe which comprises:
   a) a porous outer biocompatible case,
   b) a peripheral region within the biocompatible case that contains ligands which bind to soluble inhibitors to a mammalian immune system,
   c) an inner region which contains cancer antigens, a leukocyte fraction of a blood sample from the mammal to be treated for cancer and one or more dendritic cell inducing factors, and
   d) a biodegradable plug wherein the peripheral region and the inner region are separated by a membrane that is porous to cytokines and cytokine receptors but impervious to cells.

66. The medical implant pellet of claim 65 which is cylindrical in shape and has an outside diameter of between 0.5 and 2 mm.

67. The medical implant pellet of claim 65 wherein the cancer antigens are autologous cancer cells harvested from the mammal to be treated.

68. The medical implant pellet of claim 65 wherein the cancer cells are placed into a chamber in the inner region wherein said chamber is impervious to cells but porous to sub-cellular components.

69. The medical implant pellet of claim 65 wherein the porous outer biocompatible case comprises polymeric components that are impervious to cells but porous to sub-cellular components.

70. The medical implant pellet of claim 65 wherein the medical implant pellet is configured for administration by insertion into subcutaneous tissue with a needle and syringe.

71. The medical implant pellet of claim 65 wherein the ligands bind with one or more of the soluble inhibitors of the immune system selected from the group consisting of gangliosides, growth factors, TGF-alpha, TGF-beta and variants thereof, PDGF, EGF, IGF and variants thereof, FGF and variants thereof, VEGF, inflammatory cytokine receptors selected from the group consisting of the TNF-alpha family:

TNF-R1, TNF-R2, CD40L, NGFR, TRAIL and variants, FASL, IL-1R1, IL1R2, IL-2R, IL-3R, IL-5R, IL-6R, IL-7R, GM-CSFR, IL-9R, IL-12R, and erythropoietin receptor.

72. The medical implant pellet of claim 65 wherein the one or more dendritic cell inducing factors are selected from the group consisting of IL-4, GM-CSF, IL-10, IL-13, an IL-17 cytokine and an IL-18 cytokine.

* * * * *

UNITED STATES PATENT AND TRADEMARK OFFICE
CERTIFICATE OF CORRECTION

Page 1 of 2

PATENT NO. : 8,697,104 B2
APPLICATION NO. : 12/715052
DATED : April 15, 2014
INVENTOR(S) : Charles Knezevich et al.

It is certified that error appears in the above-identified patent and that said Letters Patent is hereby corrected as shown below:

On the Title Page
Abstract, item (57),
Line 2, "in viva" should read --in vivo--.

In the Specification
Column 2,
Line 48, "(a) a biocompatible...; (h)" should read --(a) a biocompatible...; (b)--.

Column 3,
Lines 17-18, "mammal to the treated" should read --mammal to be treated--.

Column 7,
Line 18, "e.g., huffy coat" should read --e.g., buffy coat--.

Column 8,
Line 23, "abrasive heads" should read --abrasive beads--.

Column 8,
Line 24, "abrasive heads" should read --abrasive beads--.

Column 8,
Line 35, "the heads" should read --the beads--.

Column 8,
Line 43, "the heads" should read --the beads--.

Column 8,
Lines 37-38, "his-acrylamide/" should read --bis-acrylamide/--.

Signed and Sealed this
Twenty-second Day of July, 2014

Michelle K. Lee
*Deputy Director of the United States Patent and Trademark Office*

CERTIFICATE OF CORRECTION (continued)
U.S. Pat. No. 8,697,104 B2

Column 8,
Line 64, "hound to the polymer" should read --bound to the polymer--.

Column 10,
Line 23, "is scaled at" should read --is sealed at--.

Column 11,
Line 36, "patient to the" should read --patient to be--.

In the Claims
Column 17,
Line 31, "53. Inc medical" should read --54. The medical--.